US012653218B2

(12) United States Patent
Christensen et al.

(10) Patent No.: US 12,653,218 B2
(45) Date of Patent: Jun. 16, 2026

(54) CORN SWEET STEEPING

(71) Applicant: DANISCO US INC., Palo Alto, CA (US)

(72) Inventors: Robert I Christensen, Pinole, CA (US); Jayarama K Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 818 days.

(21) Appl. No.: 17/913,941

(22) PCT Filed: Mar. 26, 2021

(86) PCT No.: PCT/US2021/024437
§ 371 (c)(1),
(2) Date: Sep. 23, 2022

(87) PCT Pub. No.: WO2021/195541
PCT Pub. Date: Sep. 30, 2021

(65) Prior Publication Data
US 2023/0131928 A1     Apr. 27, 2023

Related U.S. Application Data

(60) Provisional application No. 63/000,067, filed on Mar. 26, 2020.

(51) Int. Cl.

| | |
|---|---|
| *A23L 29/30* | (2016.01) |
| *A23D 9/04* | (2006.01) |
| *A23J 1/12* | (2006.01) |
| *A23K 10/38* | (2016.01) |
| *C12P 19/02* | (2006.01) |
| *C12P 19/14* | (2006.01) |
| *C13K 1/06* | (2006.01) |

(52) U.S. Cl.
CPC ............... *A23L 29/35* (2016.08); *A23D 9/04* (2013.01); *A23J 1/125* (2013.01); *A23K 10/38* (2016.05); *C12P 19/02* (2013.01); *C12P 19/14* (2013.01); *C13K 1/06* (2013.01)

(58) Field of Classification Search
CPC . C13K 1/06; C13K 13/00; C12P 19/14; C12P 7/06
See application file for complete search history.

(56) References Cited

U.S. PATENT DOCUMENTS

| | | | |
|---|---|---|---|
| 7,452,425 | B1 | 11/2008 | Langhauser |
| 7,842,484 | B2 | 11/2010 | Lewis |

(Continued)

FOREIGN PATENT DOCUMENTS

| | | |
|---|---|---|
| CA | 2559105 C | 9/2005 |
| CA | 2978347 C | 6/2015 |

(Continued)

OTHER PUBLICATIONS

International Search Report and Written Opinion—PCT/US2021/024437—mailed Jul. 12, 2021.

*Primary Examiner* — Elizabeth Gwartney

(57) ABSTRACT

Described is a process for releasing soluble starch hydrolysates or hydrolysed starch syrup from substantially intact corn kernels during high temperature steeping at a temperature at or above the gelatinization temperature of starch in the corn kernels, and the recovery of protein and oil-enhanced, carbohydrate-depleted residuals that are ideally suited for use as high quality animal feed or other food-grade products.

19 Claims, 1 Drawing Sheet

(56)           References Cited

U.S. PATENT DOCUMENTS

| | | |
|---|---|---|
| 7,919,291 B2 | 4/2011 | Lewis et al. |
| 8,748,141 B2 | 6/2014 | Lewis et al. |
| 9,051,538 B1 | 6/2015 | Roa-Espinosa |
| 9,375,731 B2 | 6/2016 | Dieker et al. |
| 9,516,891 B1 | 12/2016 | Roa-Espinosa |
| 9,523,104 B2 | 12/2016 | Fuchs et al. |
| 9,718,006 B2 | 8/2017 | Lee et al. |
| 9,777,303 B2 | 10/2017 | Jakel et al. |
| 10,093,891 B2 | 10/2018 | Kohl et al. |
| 10,113,007 B2 | 10/2018 | Kohl |
| 10,480,038 B2 | 11/2019 | Jakel et al. |
| 11,053,557 B2 | 7/2021 | Jakel et al. |
| 11,060,116 B2 | 7/2021 | Redford |
| 2010/0260918 A1 | 10/2010 | Wang et al. |
| 2019/0284593 A1 | 9/2019 | Jakel et al. |
| 2019/0309377 A1 | 10/2019 | Jakel et al. |
| 2021/0180100 A1 | 6/2021 | Tracy et al. |

FOREIGN PATENT DOCUMENTS

| | | |
|---|---|---|
| CA | 2875804 C | 2/2016 |
| EP | 2281898 B1 | 8/2016 |
| WO | 2013/155431 A1 | 10/2013 |
| WO | 2014/182807 A1 | 11/2014 |

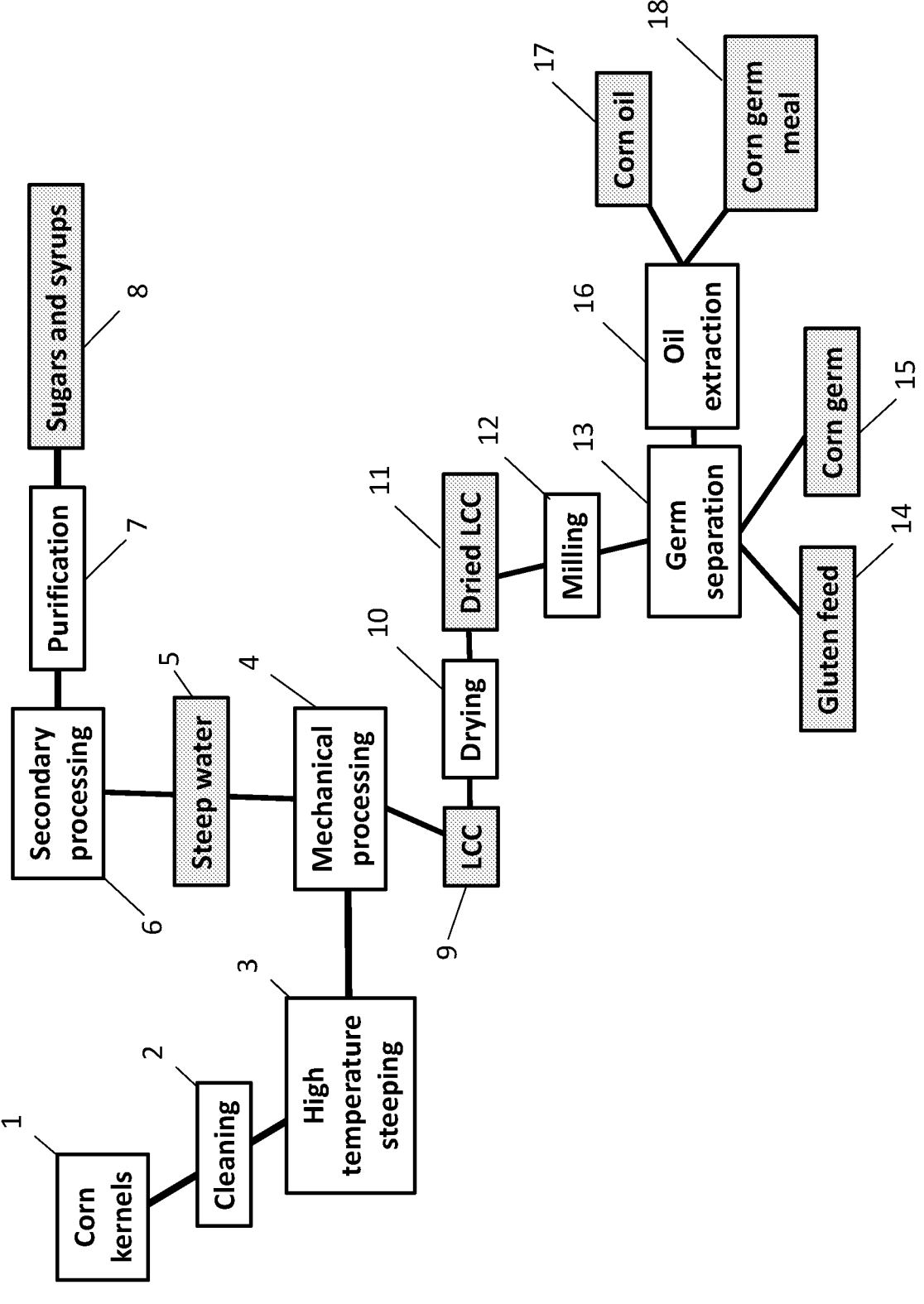

CORN SWEET STEEPING

CROSS REFERENCE

This application is a 371 of International Application No. PCT/US2021/024437, filed Mar. 26, 2021, which claims the benefit of U.S. Provisional Application No. 63/000,067, filed Mar. 26, 2020, both of which are incorporated by reference in their entirety.

FIELD OF THE INVENTION

Disclosed is a process for releasing soluble starch hydrolysates or hydrolysed starch syrups from substantially intact seeds and fruits during high temperature steeping, and the recovery of protein and oil-enhanced, carbohydrate-depleted residuals that are ideally suited for use as value added animal feed or other feed or food-grade products.

BACKGROUND

Wet milling and dry grind milling are the predominant methods for processing grains into syrups, ethanol and co-products, such as animal feed and oil. Corn is the predominant grain processed by these methods, but wheat, barley, rye, sorgum, milo, rice and the like can be processed in a similar manner.

Using corn as an example, the wet-milling process is designed to extract maximum value from each component in a corn kernel. Corn kernals are first steeped in water at about 50° C. for 36 hours with the optional addition of $SO_2$ and lactic acid. Steeping breaks disulfide bonds and weakens the gluten starch matrix, allowing for improved release of starch granules. Acid protease can be used in place of $SO_2$. The steepwater contains corn soluble solids such as salts, soluble amino acids, peptides, proteins and other micronutrients, but virtually no starch.

The softened kernels are then mechanically processed to remove the germ, which is further processed to recover high-value corn oil. Following germ removal, the remaining kernel components are screened to recover the fiber used to produce gluten feed for animals. Starch and some gluten pass through the screens and are subsequently subjected to centrifugation to separate lighter gluten protein (which can be added to the gluten meal) from starch. The starch is subjected to enyzymatic hydrolysis by α-amylase to produce hydrolyzed starch syrup which can then be converted to glucose, maltose or other sugars for the production of syrups. While such sugars can also be used as a feementation feed stocks for producing ethanol and other valuable biochemicals, they are more often into more value food products, including specialty syrups and high-fructose corn sugar.

Corn dry grind milling process is less capital intensive process that focuses primarily on the production of grain ethanol. In this process, corn kernels are first hammer milled to a medium-to-fine grind prior to enzymatic processing. Enzymatic processing occurs first with a thermostable α-amylase (optionally with protease and other enzymes) at or above the starch geletanization temperature. Processing at higher temperatures requires a jet-cooker, which is expensive capital and consumes a large amount of energy. As with wet milling, the resulting maltodextrins can then be converted to glucose, or theoretically other sugars. However, dry grind milling tends to be a process using whole ground corn for industrial grade products and is not suitable for the production of food grade products. Accordingly, fuel ethanol, dried distillers grains (a low-value animal feed product) and oil (for the production of biodiesel), tend to be the only products.

In recent years, dry grind milling fractionation processes have been modified to increase the production and recovery of higher-value co-products. However, such products are unlikely to be foodgrade and often require capital investment and the use many additional enzymes and processing steps. The need exist for superior ways to process grains to extract maximum value with minimal capital investment.

SUMMARY

Described is a process for releasing soluble starch hydrolysates or hydrolysed starch syrups from substantially intact seeds and fruits during high temperature steeping, and the recovery of protein and oil-enhanced, starch-depleted residuals that are ideally suited for use as value added animal feed or other feed or food-grade products. Aspects and embodiments of the present compositions and methods are summarized in the following, separately-numbered paragraphs:

1. In one aspect, a method for producing soluble starch hydrolysates or hydrolysed starch syrups from corn kernels is provided, comprising steeping substantially intact corn kernels in water at a temperature at or above the gelatinization temperature of starch in the corn kernels, wherein steeping is performed in the presence of an exogenous thermostable α-amylase that produces soluble starch hydrolysates or hydrolysed starch syrups from starch present in the corn kernels and the steeping temperature causes inactivation of endogenous corn proteases and carbohydrate hydrolyzing enzymes present in the corn kernels, and subsequently fractionating the steeped corn kernels to obtain a soluble starch hydrolysates or hydrolysed starch syrups fraction and a substantially intact, starch-depleted and protein and oil-enhanced corn kernel residual.

2. In some embodiments of the method of paragraph 1, the steeped corn kernels are subjected to mild press conditions to squeeze out entrapped soluble starch hydrolysates or hydrolysed starch syrups prior to fractionation.

3. In some embodiments of the method of paragraph 1 or 2, the steeped corn kernels are subjected to mild centrifugation conditions to squeeze out entrapped soluble starch hydrolysates or hydrolysed starch syrups prior to fractionation.

4. In some embodiments of the method of any of paragraphs 1-3, steeping is further performed in the presence of additional enzymes.

5. In some embodiments of the method of any of paragraphs 1-4, the soluble starch hydrolysates or hydrolysed starch syrups fraction is further contacted with additional enzymes.

6. The method of paragraph 4 or 5, wherein the additional enzymes are selected from the group consisting of glucoamylase, pullulanase, β-amylase, maltogenic α-amylase, phytase and combinations, thereof.

7. In some embodiments of the method of any of paragraphs 1-6, the soluble starch hydrolysates or hydrolysed starch syrups fraction is converted to ethanol.

8. In some embodiments of the method of any of paragraphs 1-6, the soluble starch hydrolysates or hydrolysed starch syrups are used to produced a specialty syrup.

9. In some embodiments of the method of paragraphs 1-6, the soluble starch hydrolysates or hydrolyzed starch syrups are used as fermentation feed stock for producing proteins, enzymes and/or other biochemicals.

10. In some embodiments of the method of any of paragraphs 1-6, the soluble starch hydrolysates or hydrolysed starch syrups are used to produced high-fructose corn syrup.

11. In some embodiments of the method of any of paragraphs 1-10, the starch-depleted and protein and oil-enhanced corn kernel residual is used for animal feed.

12In some embodiments of the method of any of paragraphs 1-10, the starch-depleted and protein and oil-enhanced corn kernel residual is used to produced oil and/or gluten.

13. In some embodiments of the method of any of paragraphs 1-12, high temperature steeping substantially intact corn kernels at a temperature at or above the gelatinization temperature of starch in the corn kernels is proceeded by a conventional steeping step at a conventional steeping temperature to wash away debris and impurities prior to steeping at an elevated temperature in the presence of the themostable α-amylase.

14. In some embodiments of the method of any of paragraphs 1-13, steeping substantially intact corn kernels at a temperature at or above the gelatinization temperature of starch in the corn kernels is proceeded by mechanical abrasion to improve the ingress of the themostable α-amylase into the substantially intact corn kernels.

15. In some embodiments of the method of any of paragraphs 1-14, themostable α-amylase is present in the steep water before the steep water contacts the substantially intact corn kernels.

16. In some embodiments of the method of any of paragraphs 1-15, themostable α-amylase is present in the steep water before the steep water is heated to the temperature at or above the gelatinization temperature of starch in the corn kernels.

17. In another aspect, a method for producing substantially intact starch-depleted and protein and oil-enhanced corn kernel residuals is provided, comprising steeping substantially intact corn kernels in steep water at a temperature at or above the gelatinization temperature of starch in the corn kernels, wherein steeping is performed in the presence of an exogenous thermostable α-amylase that releases soluble starch hydrolysates or hydrolysed starch syrups from starch present in the corn kernels and the temperature at or above the gelatinization temperature of starch in the corn kernels inactivates endogenous corn proteases and carbohydrate hydrolyzing enzymes present in the corn kernels, and subsequently separating soluble starch hydrolysates or hydrolysed starch syrup-containing steep water from the steeped corn kernels to obtain substantially intact, starch-depleted and protein and oil-enhanced corn kernel residuals.

18. In some embodiments of the method of paragraph 17, the starch-depleted and protein and oil-enhanced corn kernel residuals is used for animal feed.

19. In some embodiments of the method of paragraph 17 or 18, the starch-depleted and protein and oil-enhanced corn kernel residual is used to produced oil and/or gluten.

20. In another aspect, a method for producing oil and gluten from a corn kernel compositions is provided, comprising steeping substantially intact corn kernels in steep water at a temperature at or above the gelatinization temperature of starch in the corn kernels, wherein steeping is performed in the presence of an exogenous thermostable α-amylase that releases soluble starch hydrolysates or hydrolysed starch syrup from starch present in the corn kernel and the temperature at or above the gelatinization temperature of starch in the corn kernels inactivates endogenous corn proteases and carbohydrate hydrolyzing enzymes present in the corn kernels, and subsequently separating soluble starch hydrolysates or hydrolysed starch syrup-containing steep water from the steeped corn kernels to obtain substantially intact, starch-depleted and protein and oil-enhanced corn kernel residual, and fractionating the starch-depleted and protein and oil-enhanced corn kernel residual into oil and gluten fractions.

21. In some embodiments of the method of any of paragraphs 1-20, steeping is performed in the presence of a preselected amount of thermostable protease to partially hydrolyze protein present in the corn kernels and/or to produce amino acids.

These and other aspects and embodiments of the present compositions and methods will be apparent from the following description and appended Examples.

BRIEF DESCRIPTION OF THE DRAWINGS

FIG. 1 shows a process flow diagram summarizing features of the present corn sweet steeping process.

DETAILED DESCRIPTION

1. Definitions and Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the enzyme" includes reference to one or more enzymes and equivalents thereof known to those skilled in the art, and so forth.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art. The following terms are defined, below, for clarity.

1.1. Abbreviations and Acronyms

The following abbreviations/acronyms have the following meanings unless otherwise specified:

° C. degrees Centigrade
$dH_2O$ or DI deionized water
g or gm grams
hr(s) hour/hours
kg kilograms
M molar
mg milligrams
min(s) minute/minutes
mL and ml milliliters
mm millimeters mM millimolar
MW molecular weight
sec seconds
U units
v/v volume/volume
w/v weight/volume
w/w weight/weight
wt % weight percent 1.2. Definitions As used herein the term "starch" refers to any material comprised of the complex polysaccharide carbohydrates of plants, comprised of amylose and/or amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, legumes, cassava, millet, potato, sweet potato, and tapioca. After purification of the complex polysaccharide carbohydrates from the other plant components, it is called "refined starch."

As used herein, "soluble starch hydrolysates" are polysaccharides derived from insoluble starch that are soluble in water at room temperature or greater. Soluble starch hydrolysates include dextrins and malto-oligosaccharides but are low in glucose content.

As used herein, "dextrins" are linear and partially branched soluble and insoluble polysaccharides produced by the partial hydrolysis of insoluble starch.

As used herein, "malto-oligosaccharides" are linear and partially branched polysaccharides produced by the hydrolysis of insoluble starch and dextrins by acid treatment or by treatment with endo-acting carbohydrases such as α-amylase amylases.

As used herein, "maltodexrins" refers to refined malto-oligosaccharides, generally ranging from DP3 to DP20, but can be longer.

As used herein, "hydrolysed starch syrups" are polysaccharides derived from insoluble starch or soluble starch hydrolysates that are rich in short malto-oligosaccharides, e.g., DP5 and less, including glucose.

As used herein, the term "α-amylase" refers to an enzyme that is, among other things, capable of catalyzing the degradation of starch. α-amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion yielding polysaccharides containing three or more (1-4)-α-linked D-glucose units.

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptides, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 90% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

The term "endogenous" with reference to a polynucleotide or protein refers to a polynucleotide or protein that occurs naturally in the host cell.

The term "specific activity" refers to the number of moles of substrate that can be converted to product by an enzyme or enzyme preparation per unit time under specific conditions. Specific activity is generally expressed as units (U)/mg of protein.

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

The term "about" refers to ±15% to the referenced value.

2. Corn Sweet Steeping

The present invention relates to a different approach for obtaining commercially valuable products from corn kernels that requires fewer processing steps and less energy than conventional wet-milling and produces higher quality residuals and uses less energy than conventional dry grind milling. A key feature of the methods is performing steeping of whole corn kernals at a temperature at or above starch gelatinization temperature in presence of a thermostable α-amylase, unlike the conventional steeping of a whole corn at a temperature below the starch gelatinization temperature in presence of a high concentration of $SO_2$ without added enzymes.

The purpose of conventional steeping is to cause grains to soften and to weaken the gluten-starch matrix, allowing for eventual separating of starch granules for other parts of the grain. This process is carried out in the presence of $SO_2$ and lactic acid to partially hydrolyze or modify gluten and further weaken the the gluten-starch matrix. In fact, starch separation from other grain materials subsequently occurs by centrifugation, requiring that the starch material remain in a dense form to affect separation.

According to the new process, steeping is performed at or above the starch geletinization temperature at an elevated temperature of at least about 68° C., at least about 70° C., at least about 72° C., at least about 74° C., at least about 76° C., at least about 78° C., at least about 80° C., at least about 82° C., at least about 84° C., at least about 86° C., at least about 88° C. or even at least about 90° C., coordinated with contacting corn kernels with water containing thermostable α-amylase. Exemplary steeping temperatures ranges are about 70-100° C. and 80-90° C. The high steeping temperature causes the tip cap to open, allowing steep water to enter the kernal and cause it to swell. The starch in the swollen corn kernals becomes accessible to the α-amylase, which hydrolizes exposed starch chains to produce soluble starch hydrolysates. The soluble starch hydrolysates are expelled from the swollen corn kernels due to osmotic pressure-driven diffusion. The high temperature deactivates endogenous carbohydrate hydrolyzing enzymes, ensuring that uncontrolled starch hydrolysis is avoided and that the starch hydrolysis pattern is determined by the thermostable α-amylase(s) selected for using in steeping.

The high temperature also deactivates endogenous proteases, leaving corn kernel proteins intact and minimizing uncontrolled hydrolysis to peptides or free amino acids. This avoids the loss of peptides and amino acids in the steeping water and maintaining the protein content of the corn kernel residuals.

At the end of the modified high temperature steeping process, mild pressing, centrifugation or other mechanical means maybe performed to squeeze remaining soluble starch hydrolysates from the swollen corn kernels into what may now be referred to as sweet steepened water. Mild conditions are those that cause soluble starch hydrolysates to be separated from the the corn kernel residual but do not otherwise fractionate or disrupt the corn kernel residual. The sweet steepened water can be used for making fermentable sugars, sugars for the production of syrups or other products of value. The remaining starch-depleted corn kernels (alternatively referred to as low carbohydrate corn (LCC)), represent minimally modified, protein and oil-enhanced versions of the native corn kernels that are ideal for use as high quality animal feed. These starch-depleted corn kernels are rich in unhydrolyzed protein and oil and may also be fractionated used to produce other food and feed products.

The new process, herein hereferred to as "high temperature enzyme steeping" or "corn sweet steeping," may not be as efficient as conventional wet-milling or dry grind milling in terms of extracting the maximum amount of starch from corn kernels. However the equipment and energy savings outway efficiency losses with respect to stach extraction, and the high quality of protein and oil-enhanced, starch-depleted residuals is expected to open up a new markets for producers.

The thermostable α-amylases may be present in the steep water before it is contacted with the corn kernels or may be present along with the corn kernels as they are being heated in the steep water. In this manner the thermostable α-amylases are available to enter the corn kernals as they begin to swell. Alternatively, the thermostable α-amylases may be added after the steepwater in which the corn kernels are being steeped is up to a desired temperature.

While the corn kernels are substantially intact, meaning not fractionated and not milled, some damage to to the corn kernels is acceptable, if not inevitable, and will not adversely affect the method. In addition, mechanical roughening of the surface of the corn kernels may be desirable to improve the ingress of the thermostable α-amylases in to the corn kernels. Minor disruption of a portion of the corn kernels as a result of roughening can be tolerated by the method; however, the method does not rely on fractionation of the corn kernels (as in the case of wet-milling) or grinding of the corn kernels (as in the case of dry grind milling) prior to being contacted with an α-amylase, which is a point of distinction between the present method and conventional methods.

In some variations of the new method, other carbohydrate processing enzymes can be added during steeping to enhance the production of soluble starch hydrolysates or to produce hydrolysed starch syrups during steeping. Such enzymes include glucoamylase, pullulanase, β-amylase, maltogenic α-amylase isoamylase, trehalase and the like. In addition, non-polysaccharide hydrolyzing enzymes such as cellulase, glucanase, xylanase, pectinase, protease and phytase can also be included. Such enzymes should be sufficiently thermostable to withstand the steeping temperature. Alternatively, these enzymes may be added later in the steeping process, in which case that do not have to survive for the entire steeping time, or may be added to the the soluble starch hydrolysates or hydrolysed starch syrups fraction after the sweet steepened water cools, in which they may not have to be thermostable.

The cooled sweet steepened water may also be saccharified, fermented, subjected to simultaneous sacchrification and fermentation (SSF), used to produce glucose or specialty syrups, used to produce high-fructose-corn syrup, used to produce ethanol or used in any conventional manner described in the art. The starch-depleted and protein and oil-enhanced corn kernel residuals can used directly as animal feed or further processed into oil, gluten or other fractionated products. Importantly, the present methods are based in the manner in which soluble starch hydrolysates or hydrolysed starch syrups are prepared from corn kernels, not the use of the end products.

A significant advantage of the present high temperature enzymatic steeping process is that the elevated steeping temperature, at or above the gelatinization temperature of starch in the corn kernels, inactivates endogenous proteases, leaving proteins intact for feeding to animals or preparing foodstuffs. However, in some variations of the new process, endogenous proteases are not entirely inactivated, or selected proteases, including thermostable proteases, are deliberately added in amount to aid release of starch from the swollen corn kernels, to supplement the sweet steepened water with amino acids for subsequent use by a fermenting organism, to modify seed or fruit proteins in a predetermined and controlled manner.

Additional processing steps may be included to improve the quality of the corn kernels used in corn sweet steeping, including washing the substantially intact kernels with water, sifting the kernals to remove debris, incubating the kernals in the presence of low amounts of enzymes such that the features of the new method are not defeated, or even incubating the kernels under conventional wet milling steep conditions (i.e., below the geletinization temperature of starch in the corn kernels).

Corn sweet steeping can be further described with reference to the process flow diagram shown in FIG. 1. In the diagram, process steps are indicated by white boxes and products or process intermediates are indicated by grey boxes.

Substantially intact corn kernels 1 are optionally subjected to a cleaning step 2 to remove debris and contaminants. The cleaning step may resemble a conventional wet mill steeping process, and is performed at a relatively low temperature that is well below the starch gelatinization temperature of the starch in the corn kernels. The corn kernels are then subjected to steeping 3 at an elevated temperature, at or above the starch gelatinization temperature of the starch in the corn kernels, in the presence of a thermostable α-amylase. During this step insoluble starch in the corn kernels are converted into soluble starch hydrolysates, or hydrolysed starch syrups, depending on whether additional starch hydrolyzing are additionally added. Optionally, a mechanical processing step 4, such as pressing and/or centrifugation, is performed to assist in expelling these hydrolysates into the steep water 5. The steep water may be subjected to secondary processing 6 with additional enzymes to convert the soluble starch hydrolysates, or hydrolysed starch syrups into desired carbohydrate products, such as glucose, maltose, high-fructose corn syrup, specialty syrups and the like, which are optionally subjected to purification 7 by, e.g., filtration, centrifugation or ion exchange, to produce desired sugars and syrups 8, which can be used for myriad purposes including, food or feed applications, as feedstocks to enzymatically produce enzymes and other valuable proteins, and to make other valuable biochemicals by way of further metabolic, enzymatical or synthetic chemical modification.

Following high temperature steeping and optional mechanical processing, low carbohydrate corn (LCC; also referred to as protein and oil-enhanced corn residuals) 9 may be used directly for animal feed, or subjected to drying 10 to produce dried LLC 11 for use as animal feed or for further processing. Further processing typically means milling 12 and germ separation 13 to produce gluten feed 14 and corn germ 15. Germ separation may be followed by oil extraction 16 to produce corn oil 17 and corn germ meal 18. The corn oil can be sulfite-free, unlike corn oil; produced using a typical wet mill process.

3. Enzymes for Use in Corn Sweet Steeping Enzymes for use in high temperature steeping include but are not limited to all thermostable α-amylase that have been described for use in wet and dry grind milling. Such enzymes include bacterial enzymes, such as SPEZYME®-AA, SPEZYME®-Alpha, SPEZYME®-Ethyl, SPEZYME®-Fred, SPEZYME®-Xtra and SPEZYME®-RSL, CLARASE™ L, GZYME™ 997 and GC356 (DuPont), TERMAMYL™ 120-L, TERMAMYL™ LC and TERMAMYL™ SC and SUPRA, LIQUOZYME™ X, SAN™ SUPER, LPHERA® and FORTIVA® (Novozymes A/S), and FUELZYME™ LF (Diversa). In some embodiments, the thermostable α-amylase will be derived from *Bacillus stearothermophilus, B. licheniformis, B. amyloliquifaciens*, a *Cytophaga* sp., or from a hybrid molecules based on one or more of these enzymes or other enzymes. Commercially-available thermostable fungal amylases include GC626® (DuPont) from *Aspergillus kawachii.*

Commercially-available thermostable glucoamylase enzymes include EXTENDA® and SPIRIZYME® (Novozymes). In some embodiments, the thermostable glucoamylase will be derived from an organism such as a *Talaromyces* sp., *Clostridium* sp. or a *Penicillium* sp.

Commercially-available thermostable phytase enzymes include AXTRA® PHY (DuPont) and RONOZYME® (Novozymes). In some embodiments, the thermostable phytase will be derived from an organism such as *Buttiauxella* sp., a *Citrobacter* sp, an *Escherichia* sp., a *Peniophora* sp. or an *Obesumbacterium* sp.

Commercially-available thermostable protease enzymes include DCO+® (DuPont) and AVENTEC® AMP (Novozymes). In some embodiments, the thermostable protease will be derived from an organism such as a *Thermobifida* sp., a *Nocardiopsis* sp., a *Thermococcus* sp. a *Streptomyces* sp. or a *Pyrococcus* sp. A classic thermostable protease is thermolysin, a neutral metalloproteinase produced by the Gram-positive bacteria *Bacillus thermoproteolyticus.*

All references cited herein are herein incorporated by reference in their entirety for all purposes.

The invention claimed is:

1. A method for producing soluble starch hydrolysates or hydrolysed starch syrups from corn kernels, comprising steeping substantially intact corn kernels in water at a temperature at or above the gelatinization temperature of starch in the corn kernels, wherein steeping is performed in the presence of an exogenous thermostable α-amylase that produces-soluble starch hydrolysates or hydrolysed starch syrups from starch present in the corn kernels and the steeping temperature is between 83-90° C. and causes inactivation of endogenous corn proteases and carbohydrate hydrolyzing enzymes present in the corn kernels, and subsequently fractionating the steeped corn kernels to obtain a soluble starch hydrolysates or hydrolysed starch syrups fraction and a substantially intact, starch-depleted and protein and oil-enhanced corn kernel residual.

2. The method of claim 1, wherein the steeped corn kernels are subjected to mild press conditions to squeeze out entrapped soluble starch hydrolysates or hydrolysed starch syrups prior to fractionation.

3. The method of claim 1, wherein the steeped corn kernels are subjected to mild centrifugation conditions to squeeze out entrapped soluble starch hydrolysates or hydrolysed starch syrups prior to fractionation.

4. The method of claim 1, wherein steeping is further performed in the presence of additional enzymes.

5. The method of claim 1, wherein the soluble starch hydrolysates or hydrolysed starch syrups fraction is further contacted with additional enzymes.

6. The method of claim 4, wherein the additional enzymes are selected from the group consisting of glucoamylase, pullulanase, β-amylase, maltogenic α-amylase, phytase and combinations, thereof.

7. The method of claim 1, wherein the soluble starch hydrolysates or hydrolysed starch syrups fraction is converted to ethanol.

8. The method of claim 1, wherein the soluble starch hydrolysates or hydrolysed starch syrups are used to produce a specialty syrup.

9. The method of claim 1, wherein the soluble starch hydrolysates or hydrolyzed starch syrups are used as fermentation feed stock for producing proteins, enzymes and/or other biochemicals.

10. The method of claim 1, wherein the soluble starch hydrolysates or hydrolysed starch syrups are used to produce high-fructose corn syrup.

11. The method of claim 1, wherein the starch-depleted and protein and oil-enhanced corn kernel residual is used for animal feed.

12. The method of claim 1, wherein the starch-depleted and protein and oil-enhanced corn kernel residual is used to produced oil and/or gluten.

13. The method of claim 1, wherein themostable a-amylase is present in the water present in the steeping process before the steep water contacts the substantially intact corn kernels.

14. The method of claim 1, wherein themostable α-amylase is present in the steep water before the steep water is heated to the temperature at or above the gelatinization temperature of starch in the corn kernels.

15. The method of claim 1, wherein steeping is performed in the presence of a preselected amount of thermostable protease to partially hydrolyze protein present in the corn kernels and/or to produce amino acids.

16. A method for producing substantially intact starch-depleted and protein and oil-enhanced corn kernel residuals, comprising steeping substantially intact corn kernels in steep water at a temperature at or above the gelatinization temperature of starch in the corn kernels, wherein steeping is performed in the presence of an exogenous thermostable a-amylase that releases soluble starch hydrolysates or hydrolysed starch syrups from starch present in the corn kernels and the temperature is between 83-90° C. and at or above the gelatinization temperature of starch in the corn kernels inactivates endogenous corn proteases and carbohydrate hydrolyzing enzymes present in the corn kernels, and subsequently separating soluble starch hydrolysates or hydrolysed starch syrup-containing steep water from the steeped corn kernels to obtain substantially intact, starch-depleted and protein and oil-enhanced corn kernel residuals.

17. The method of claim 16, wherein the starch-depleted and protein and oil-enhanced corn kernel residuals is used for animal feed.

18. The method of claim 16, wherein the starch-depleted and protein and oil-enhanced corn kernel residual is used to produce oil and/or gluten.

19. A method for producing oil and gluten from a corn kernel compositions, comprising steeping substantially intact corn kernels in steep water at a temperature at or above the gelatinization temperature of starch in the corn kernels, wherein steeping is performed in the presence of an exogenous thermostable a-amylase that releases soluble starch hydrolysates or hydrolysed starch syrup from starch present in the corn kernel and the temperature is between 83-90° C. and at or above the gelatinization temperature of starch in the corn kernels inactivates endogenous corn proteases and carbohydrate hydrolyzing enzymes present in the corn kernels, and subsequently separating soluble starch hydrolysates or hydrolysed starch syrup-containing steep water from the steeped corn kernels to obtain substantially intact, starch-depleted and protein and oil-enhanced corn kernel residual, and fractionating the starch-depleted and protein and oil-enhanced corn kernel residual into oil and gluten fractions, and wherein steeping is performed in the presence of a preselected amount of thermostable protease to partially hydrolyze protein present in the corn kernels and/or to produce amino acids.

* * * * *